United States Patent
Marash et al.

(10) Patent No.: US 11,259,760 B2
(45) Date of Patent: Mar. 1, 2022

(54) APPARATUS AND METHOD FOR PROVIDING PATIENT IMAGING

(71) Applicant: P-Cure, Ltd., Lod (IL)

(72) Inventors: Michael Marash, Rishon Le'tzion (IL); Michael Shpunt, Ramle (IL)

(73) Assignee: P-CURE LTD., Lod (IL)

( * ) Notice: Subject to any disclaimer, the term of this patent is extended or adjusted under 35 U.S.C. 154(b) by 1607 days.

(21) Appl. No.: 14/426,750

(22) PCT Filed: Sep. 29, 2013

(86) PCT No.: PCT/IL2013/050804
§ 371 (c)(1),
(2) Date: Mar. 8, 2015

(87) PCT Pub. No.: WO2014/049597
PCT Pub. Date: Apr. 3, 2014

(65) Prior Publication Data
US 2015/0208992 A1    Jul. 30, 2015

Related U.S. Application Data

(60) Provisional application No. 61/706,791, filed on Sep. 28, 2012.

(51) Int. Cl.
*A61B 6/04* (2006.01)
*A61B 6/03* (2006.01)
(Continued)

(52) U.S. Cl.
CPC .......... *A61B 6/0487* (2020.08); *A61B 6/032* (2013.01); *A61B 6/0478* (2013.01);
(Continued)

(58) Field of Classification Search
None
See application file for complete search history.

(56) References Cited

U.S. PATENT DOCUMENTS 5,954,647 A * 9/1999 Bova ................ A61B 6/035
600/407
2004/0184579 A1 9/2004 Mihara et al.
(Continued)

FOREIGN PATENT DOCUMENTS

WO    2006124434 A2    11/2006

OTHER PUBLICATIONS

International Search Report for PCT/IL2013/050804 mailed by Israel Patent Office dated Jan. 23, 2014.
(Continued)

*Primary Examiner* — Jonathan Cwern
(74) *Attorney, Agent, or Firm* — The Roy Gross Law Firm, LLC; Roy Gross

(57) ABSTRACT

A method of providing imaging of a patient supported by a patient support platform arranged to be rotated about a first patient rotation axis by a patient rotation angle, the method constituted of: rotating an imager about an imager rotation axis by the patient rotation angle; translating the imager along a first imager translation axis; and translating the imager along a second imager translation axis different than the first imager translation axis, wherein responsive to the translation of the imager along the first imager translation axis and along the second imager translation axis, the imager is translated along an imaging axis defined by the patient support platform such that the imager is arranged to image the patient supported by the patient support platform.

18 Claims, 13 Drawing Sheets

(51) Int. Cl.
 *A61B 6/00* (2006.01)
 *A61N 5/10* (2006.01)

(52) U.S. Cl.
 CPC .......... *A61B 6/4464* (2013.01); *A61B 6/4476* (2013.01); *A61N 5/1071* (2013.01); *A61N 2005/1063* (2013.01)

(56) References Cited

U.S. PATENT DOCUMENTS

| | | | |
|---|---|---|---|
| 2005/0058257 A1* | 3/2005 | Fischer | A61B 6/04 378/196 |
| 2005/0201510 A1* | 9/2005 | Mostafavi | A61B 5/113 378/8 |
| 2007/0215819 A1* | 9/2007 | Hiramoto | A61N 5/1049 250/492.3 |
| 2008/0292053 A1 | 11/2008 | Marash et al. | |
| 2008/0317216 A1 | 12/2008 | Lifshitz et al. | |
| 2009/0024025 A1* | 1/2009 | Maschke | A61B 6/505 600/425 |
| 2010/0069920 A1 | 3/2010 | Naylor et al. | |
| 2013/0051518 A1* | 2/2013 | Laukkanen | A61B 6/035 378/4 |
| 2014/0056403 A1* | 2/2014 | Marash | A61B 6/03 378/20 |

OTHER PUBLICATIONS

Written Opinion of the International Searching Authority for PCT/IL2013/050804 mailed by Israel Patent Office dated Jan. 23, 2014.
Office Action from Chinese Patent Office for parallel application 201380051053.X dated Nov. 30, 2016.

* cited by examiner

| | |
|---|---|
| 1000 | ROTATE AN IMAGER ABOUT IMAGER ROTATION AXIS BY PATIENT ROTATION ANGLE OF PATIENT SUPPORT PLATFORM ROTATED ABOUT FIRST PATIENT ROTATION AXIS, OPTIONALLY AT LEAST 30 DEGREES, OPTIONALLY IMAGER ONE OF: CLOSED RING CT; OPEN RING CT; AND C-ARM CT |
| 1010 | TRANSLATE IMAGER ALONG FIRST IMAGER TRANSLATION AXIS |
| 1020 | TRANSLATE IMAGER ALONG DIFFERENT SECOND IMAGER TRANSLATION AXIS, OPTIONALLY CONTEMPORANEOUSLY WITH TRANSLATION ALONG FIRST IMAGER TRANSLATION AXIS, THEREBY IMAGER TRANSLATED ALONG IMAGING AXIS DEFINED BY PATIENT SUPPORT PLATFORM SUCH THAT IMAGER IS ARRANGED TO IMAGE PATIENT |
| 1030 | (OPT.) ROTATE PATIENT SUPPORT PLATFORM ABOUT FIRST PATIENT ROTATION AXIS |
| 1040 | (OPT.) ROTATE PATIENT SUPPORT PLATFORM ABOUT SECOND PATIENT ROTATION AXIS, GENERALLY ORTHOGONAL WITH FIRST PATIENT ROTATION AXIS |
| 1050 | (OPT.) TRANSLATE PATIENT SUPPORT PLATFORM FROM FIRST PATIENT POSITION TO SECOND PATIENT POSITION IN RELATION TO TREATMENT SOURCE, SECOND PATIENT POSITON REMOVED FROM FIRST PATIENT POSITION BY AT LEAST TWO DIMENSIONS |
| 1060 | (OPT.) TRANSLATE IMAGER ALONG ONE OF FIRST IMAGER TRANSLATION AXIS AND SECOND IMAGER TRANSLATION AXIS FROM A FIRST IMAGER POSITION TO A SECOND IMAGER POSITION, THE IMAGER ARRANGED TO INTERSECT THE IMAGING AXIS IN THE SECOND IMAGER POSITION |

FIG. 3

APPARATUS AND METHOD FOR PROVIDING PATIENT IMAGING

TECHNICAL FIELD OF THE INVENTION

The invention relates generally to the field of teletherapy and in particular to a method and apparatus for evaluating a change in radiation distribution within a target tissue.

BACKGROUND OF THE INVENTION

Teletherapy is defined as a treatment methodology in which an irradiation source is at a distance from the body to be treated. X-rays and electron beams have long been used in teletherapy to treat various cancers. Unfortunately, X-rays exhibit a linear energy transfer approaching an exponential attenuation function, and are therefore of minimal safe use for deeply embedded growths. The use of heavy particles, particularly hadrons and more particularly protons, in teletherapy has found increasing acceptance, due to the ability of heavy particles to penetrate to a specific depth without appreciably harming intervening tissue. In particular, the linear energy transfer of hadrons exhibits an inversed depth profile with a marked Bragg peak defined as the point at which the hadrons deposit most of their energy, and occurs at the end of the hadrons path. As a result of this effect, increased energy can be directed at an embedded growth as compared to X-rays and electron beams, which particularly harm intervening tissues. While the term hadrons include a wide range of particles, practically, protons and various ions are most widely used in therapy. For clarity, this document will describe treatment as being accomplished with protons, however this is not meant to be limiting in any way.

The charged protons or ions can be focused to a target volume of variable penetration depth. In this way the dose profile can be matched closely to the target volume with a high precision. In order to ensure complete irradiation of the target growth, a plurality of beams arriving at the embedded growth from several different directions is preferred. The point at which the plurality of beams intersects, whether they are beamed sequentially or simultaneously, is termed the isocenter, and to maximize biological effectiveness the isocenter must be precisely collocated with the target growth.

Irradiation treatment is performed on a target tissue in a well defined process. In a first stage, known as the treatment planning stage, the target tissue is imaged and a treatment plan comprising dosage, patient position, and irradiation angles are defined. Furthermore, placement markers are defined, so as to ensure that subsequent irradiation sessions are properly targeted. Irradiation is then performed, responsive to the developed treatment plan, at a plurality of treatment sessions over a period of time, each session being known as a fraction.

Unfortunately, the necessary treatment position can be varied to a great degree, yet current CT imagers are limited in their degree of movement. Therefore, utilizing current CT imagers does not allow imaging a patient in the planned treatment position. Disadvantageously, a change in the position of the patient can cause a change in the position of one or more organs and/or tissues within the body. Thus, when the patient is imaged in a position restricted by the movement restrictions of the CT imager, the image may not accurately present the position of the target tissue when in the treatment position.

Additionally, at each fraction, care must be taken to ensure proper patient positioning, responsive to the placement markers, so as to avoid damage to organs in vicinity of the target tissue. Positioning of the patient responsive to the markers is typically performed based on visualization of the patient, responsive to the defined markers. Disadvantageously, positioning based on visualization is not always accurate. Imaging the patient prior to treatment, such as with a computed tomography (CT) imager, would be advantageous as it would provide more accurate positioning of the target tissue in relation to the irradiation treatment source. Unfortunately, as described above, utilizing current CT imagers does not allow imaging the patient in the planned treatment position and thus a shift may occur in the position of the patient during the movement from the imaging position in relation to the CT imager to the planned treatment position.

There is thus a long felt need for an improved treatment arrangement which provides for imaging of a patient target tissue while in the planned treatment position, thereby allowing for greater accuracy in the patient imaging and treatment planning.

SUMMARY OF THE INVENTION

Accordingly, it is a principal object of the present invention to overcome disadvantages of prior art methods and arrangements of patient imaging. In one embodiment, an apparatus is provided for providing imaging of a patient supported by a patient support platform, the patient support platform arranged to be rotated about a first patient rotation axis by a patient rotation angle, the apparatus comprising: an imager; an imager positioner in communication with the imager and arranged to rotate the imager about an imager rotation axis; a first imager translation mechanism arranged to translate the imager along a first imager translation axis; a second imager translation mechanism arranged to translate the imager along a second imager translation axis different than the first imager translation axis; and a control circuitry in communication with the imager positioner and arranged to: control the imager positioner to rotate the imager about the imager rotation axis by the patient rotation angle; control the first imager translation mechanism to translate the imager along the first imager translation axis; and control the second imager translation mechanism to translate the imager along the second imager translation axis, wherein responsive to the translation of the imager along the first imager translation axis and along the second imager translation axis, the imager is translated along an imaging axis defined by the patient support platform such that the imager is arranged to image the patient supported by the patient support platform.

In one embodiment, the imaging apparatus further comprises: the patient support platform; and a patient support positioner in communication with the patient support platform and arranged to rotate the patient support platform about the first patient rotation axis, wherein the control circuitry is further arranged to control the patient support positioner to rotate the patient support platform about the first patient rotation axis by the patient rotation angle. In one further embodiment, the imaging apparatus further comprises a patient support translation mechanism arranged to translate the patient support platform from a first patient position to any of a plurality of second patient positions such that the patient supported by the patient support platform is in a predetermined position in relation to an irradiation source, wherein, in the second patient position, the patient support platform is removed from the first patient position in at least two dimensions, wherein, prior to the translation of the imager along the imaging axis, the control circuitry is further arranged to control one of the first imager translation mechanism and the second imager translation mechanism to translate the imager from a first imager position to a second imager position, wherein, in the second imager position, the imager is arranged to intersect the imaging axis.

In one yet further embodiment, the patient support positioner is further arranged to rotate the patient support platform about a second patient rotation axis generally orthogonal to the first patient rotation axis. In another embodiment, the translation of the imager along the first imager translation axis is contemporaneous with the translation of the imager along the second imager translation axis.

In one embodiment, the first patient rotation axis is at least 30 degrees. In another embodiment, the imager comprises one of: a close ring computed tomography imager; an open ring computed tomography imager; and a C-arm computed tomography imager.

In one embodiment, the control circuitry is further arranged to control the imager to image the patient contemporaneously with the translation along the imaging axis. In another embodiment, the control circuitry is further arranged to alternately: control the first imager translation mechanism and the second imager translation mechanism to translate the imager along the imaging axis by a predetermined distance; and control the imager to image the patient.

In one embodiment, the control circuitry is further arranged to alternately: control the first imager translation mechanism to translate the imager along the first imager translation axis; control the imager to image the patient; control the second imager translation mechanism to translate the imager along the second imager translation axis; and control the imager to image the patient.

In one independent embodiment, a method of providing imaging of a patient supported by a patient support platform arranged to be rotated about a first patient rotation axis by a patient rotation angle is provided, the method comprising: rotating an imager about an imager rotation axis by the patient rotation angle; translating the imager along a first imager translation axis; and translating the imager along a second imager translation axis different than the first imager translation axis, wherein responsive to the translation of the imager along the first imager translation axis and along the second imager translation axis, the imager is translated along an imaging axis defined by the patient support platform such that the imager is arranged to image the patient supported by the patient support platform.

In one embodiment, the method further comprises rotating the patient support platform about the first patient rotation axis by the patient rotation angle. In another embodiment, the translating the imager along the first imager translation axis is contemporaneous with the translating the imager along the second imager translation axis.

In one embodiment, the patient rotation angle is at least 30 degrees. In another embodiment, the method further comprises: translating the patient support platform from a first patient position to any of a plurality of second patient positions, such that the patient supported by the patient support platform is in a predetermined position in relation to an irradiation treatment source; and prior to the translating the imager along the imaging axis, translating the imager along one of the first imager translation axis and the second imager translation axis from a first imager position to a second imager position, wherein, in the second patient position, the patient support platform is removed from the first patient position in at least two dimensions, and wherein, in the second imager position, the imager is arranged to intersect the imaging axis. In one further embodiment, the method further comprises rotating the patient support platform about a second patient rotation axis generally orthogonal to the first patient rotation axis.

In another embodiment, the imager comprises one of: a closed ring computed tomography imager; an open ring computed tomography imager; and a c-arm computed tomography imager. In one embodiment, the method further comprises imaging the patient contemporaneously with the translating along the imaging axis.

In another embodiment, the method further comprises alternately: translating the imager along the imaging axis by a predetermined distance; and imaging the patient. In one embodiment, the method further comprises alternately: translating the imager along the first imager translation axis; imaging the patient; translating the imager along the second imager translation axis; and imaging the patient.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 3 illustrates a high level flow chart of a method of providing imaging of a patient supported by a patient support platform.

DETAILED DESCRIPTION OF THE PREFERRED EMBODIMENTS

Figure 1A:
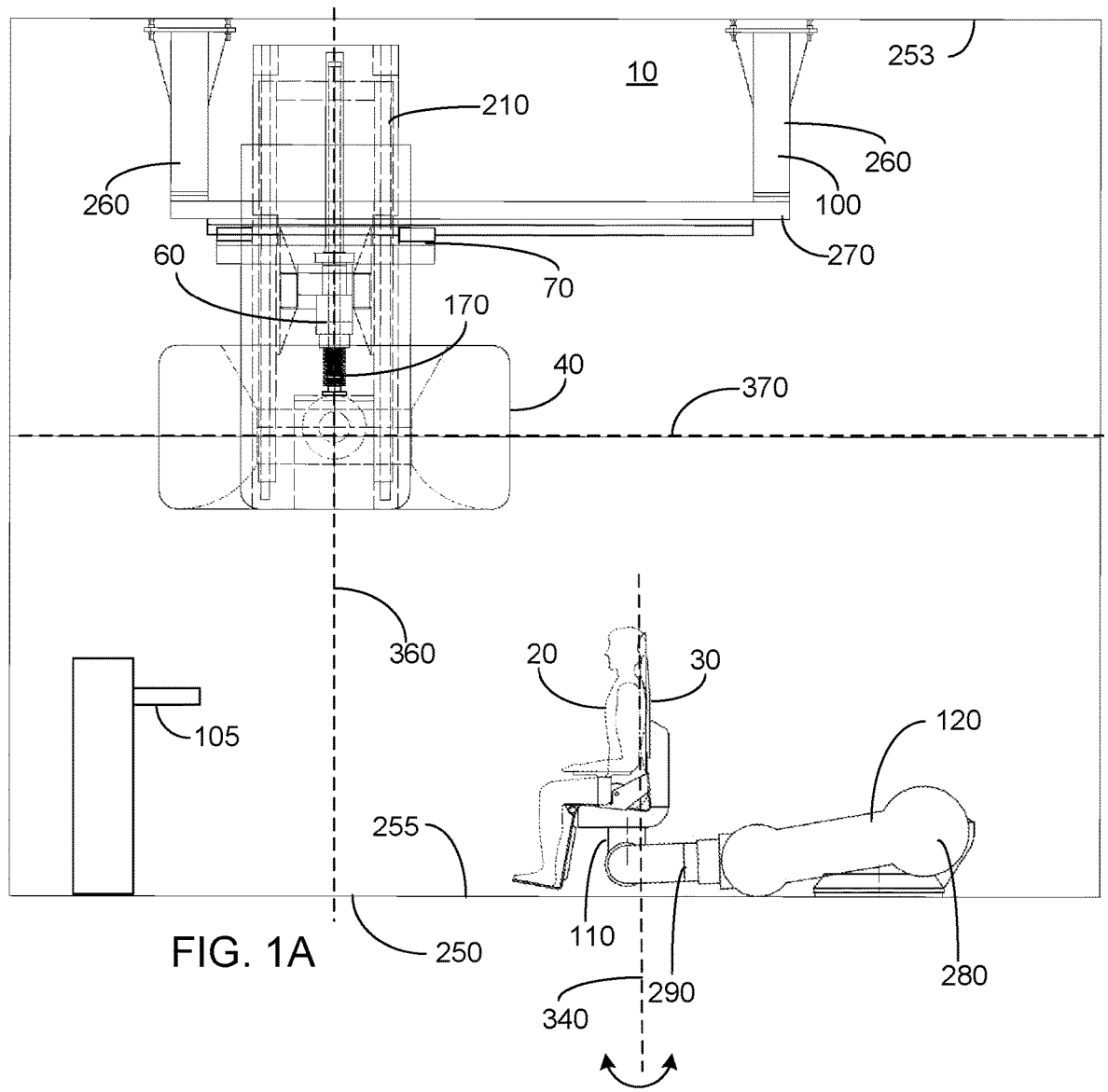
FIGS. 1A-1F illustrate a high level schematic diagram of various positions a first embodiment of an imaging apparatus for use with a patient supported by a patient support platform.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1B:
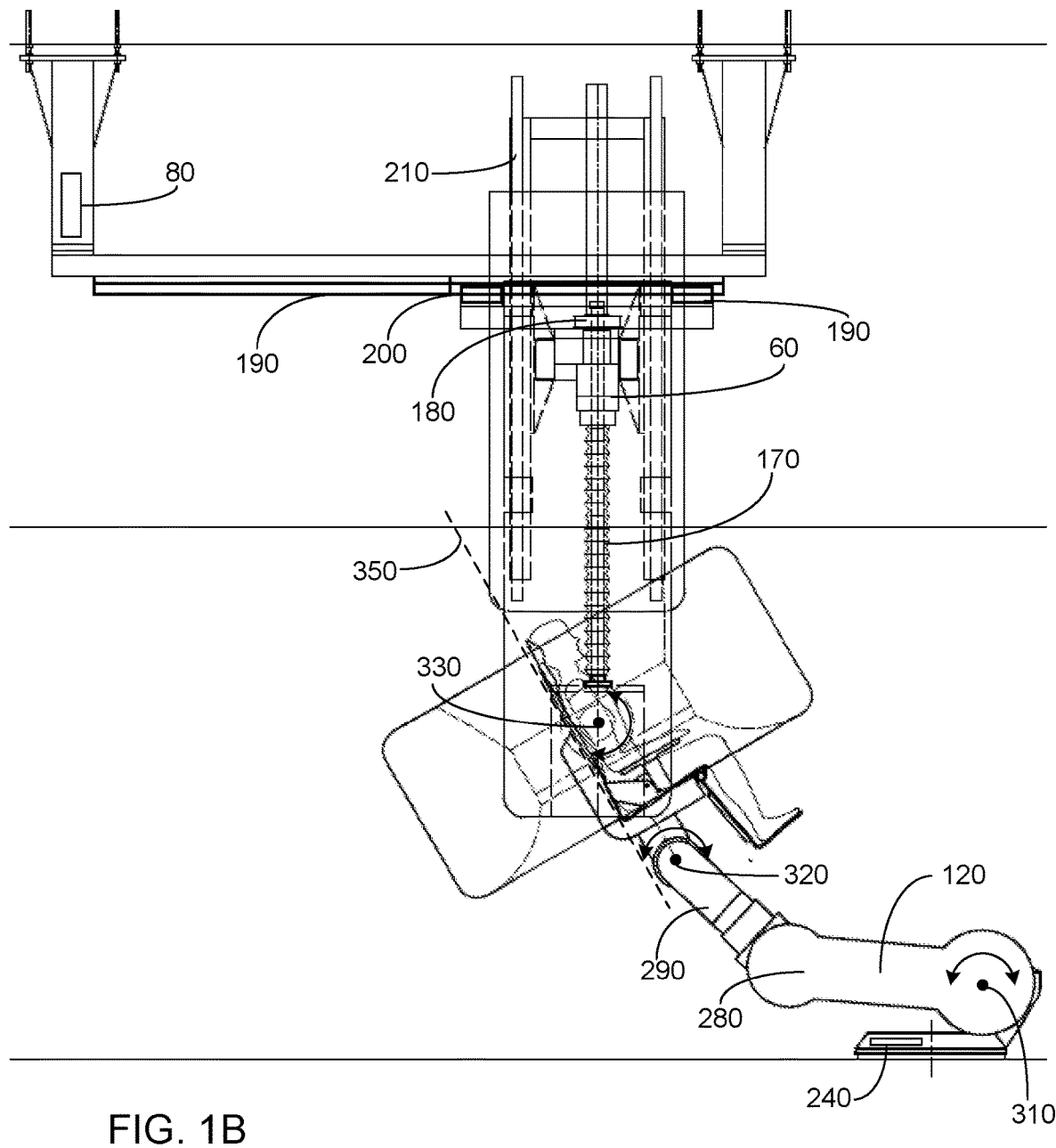
Figure 1C:
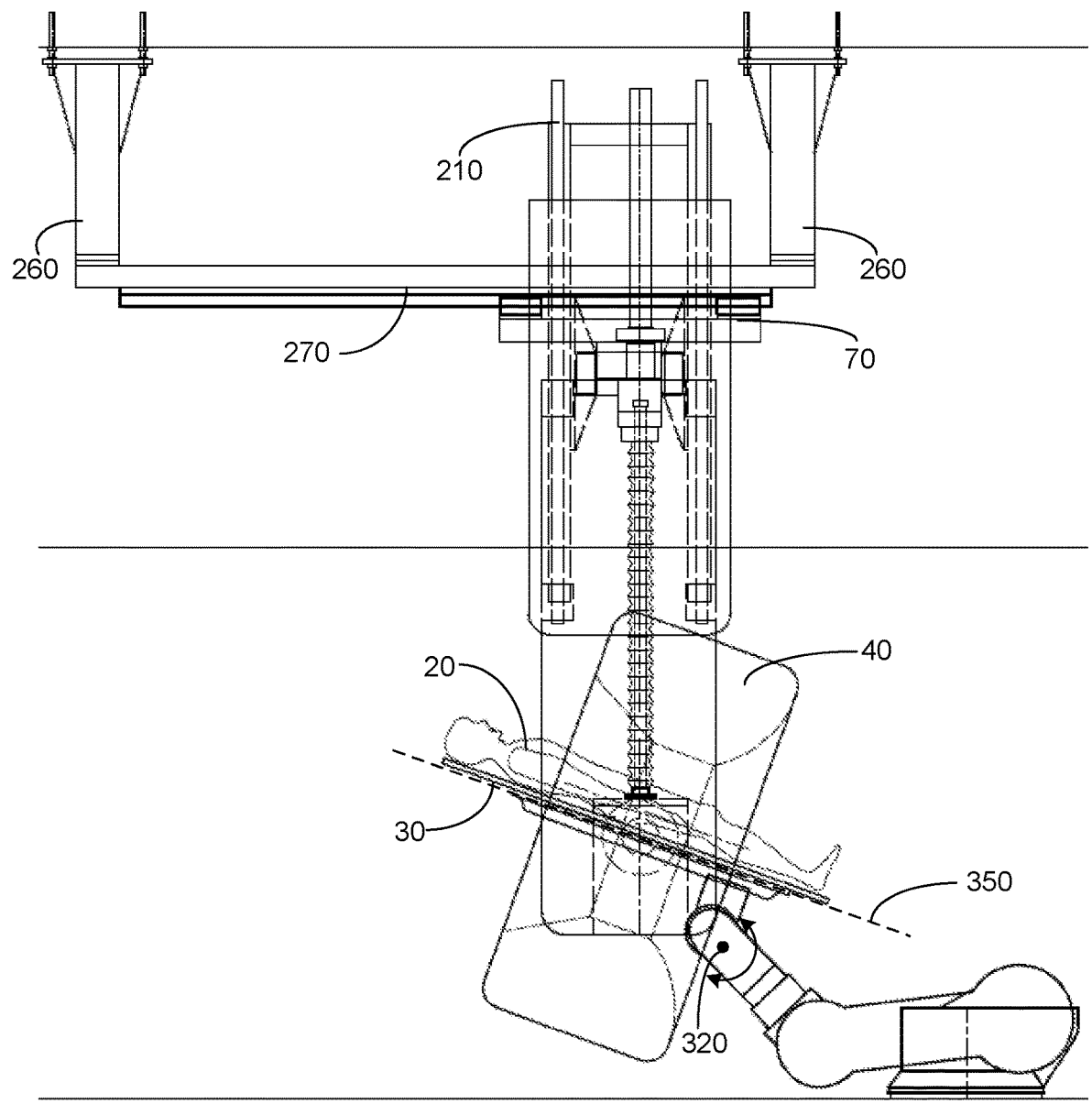
Figure 1D:
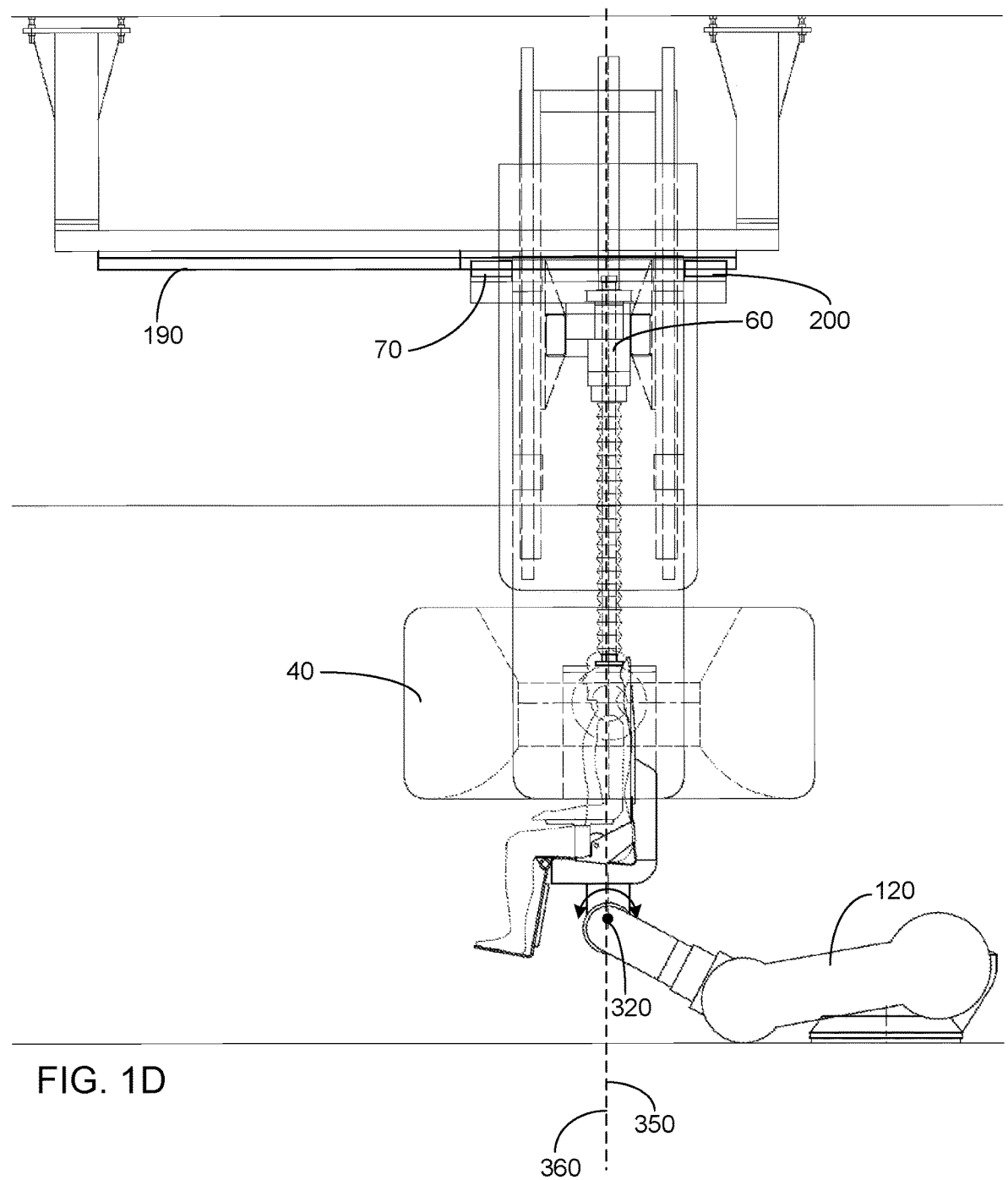
Figure 1E:
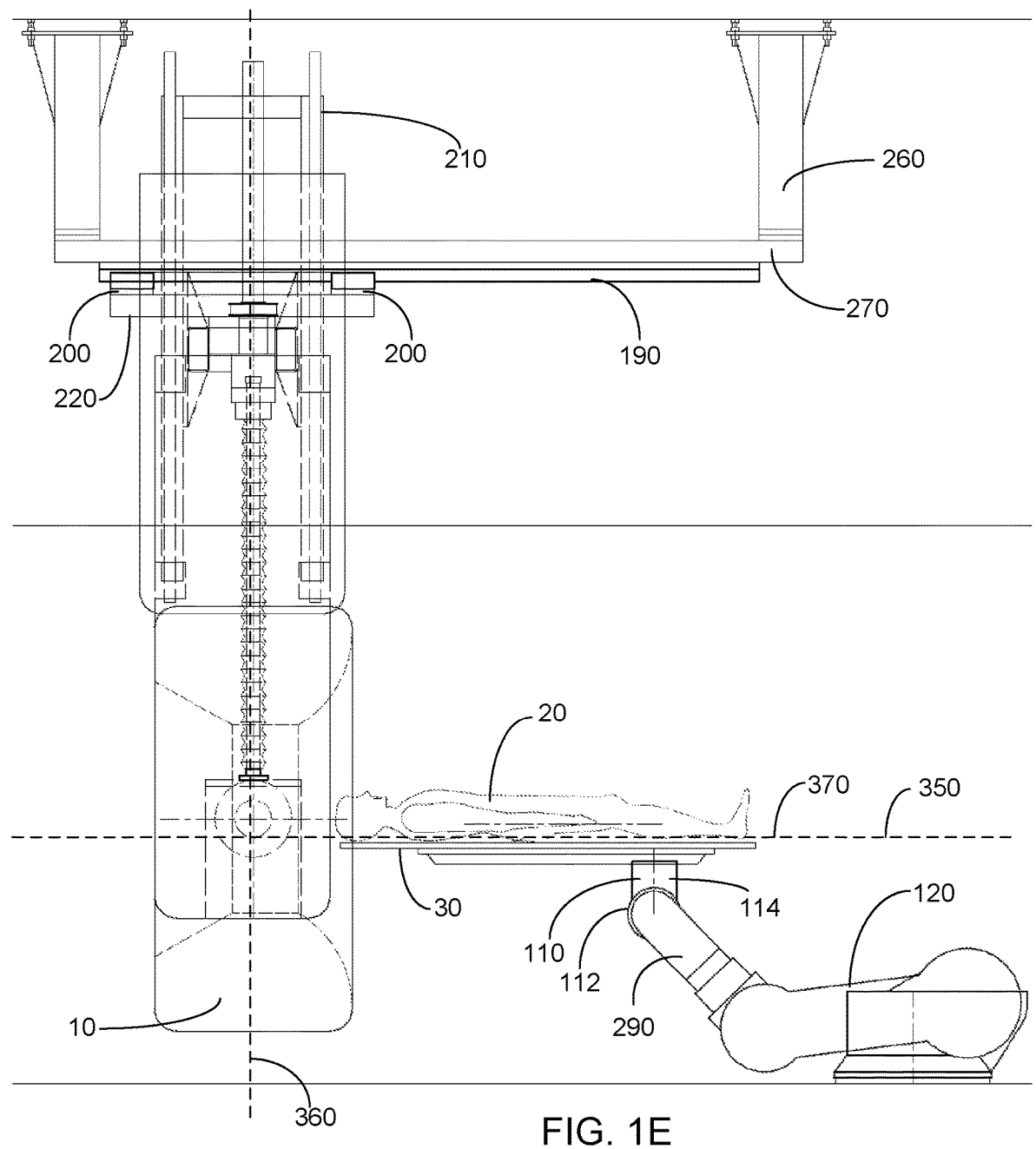
Figure 1F:
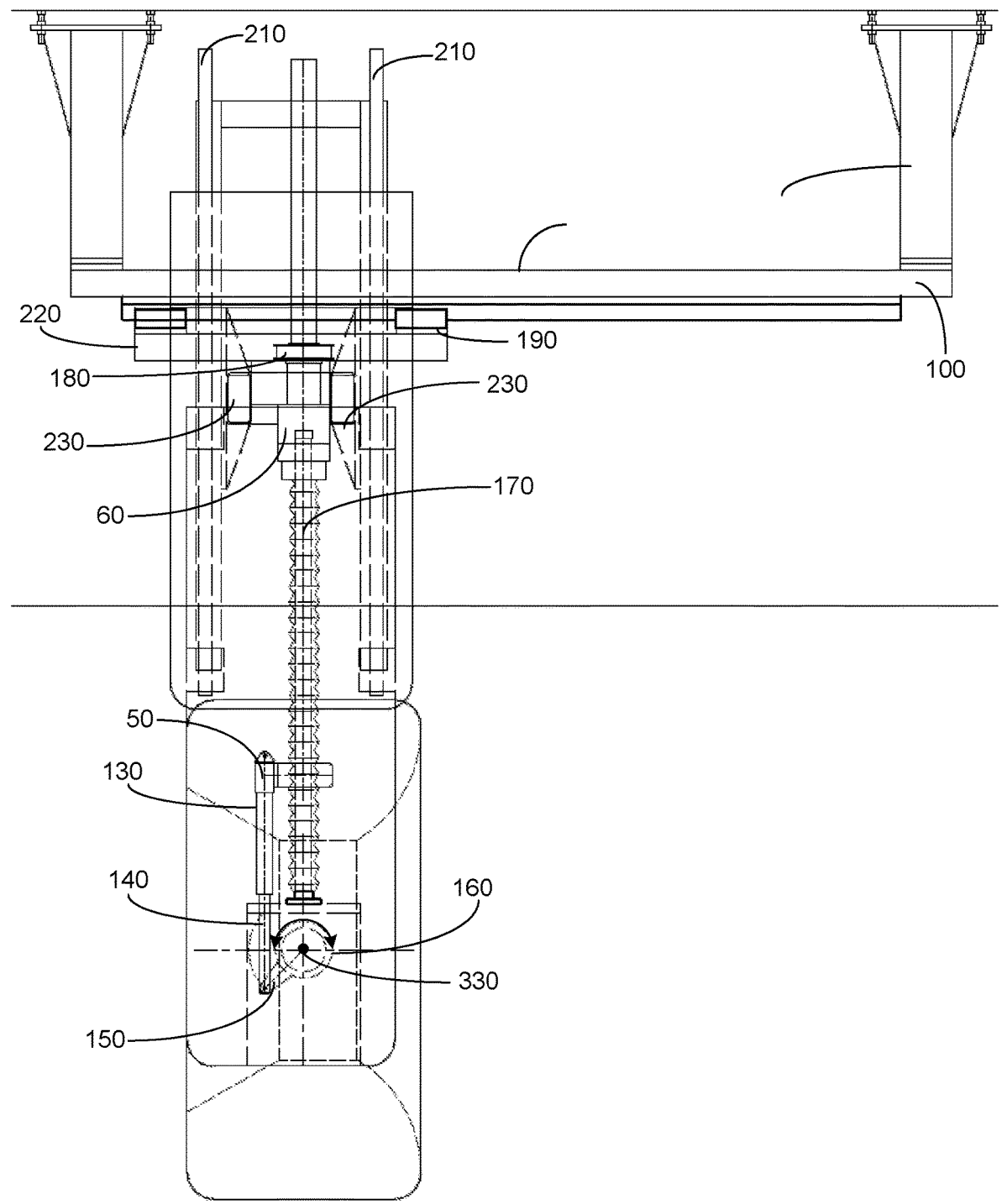

FIG. 1A illustrates a high level schematic diagram of an imaging imaging apparatus 10 for use with a patient 20 supported by a patient support platform 30, patient 20 illustrated in a seated position and imaging apparatus 10 in a contracted position; FIG. 1B illustrates a high level schematic diagram of imaging apparatus 10, with patient 20 illustrated in a tilted seated position and imaging apparatus 10 in an imaging position; FIG. 1C illustrates a high level schematic diagram of imaging apparatus 10, with patient 20 illustrated in a tilted supine position and imaging apparatus 10 in an imaging position; FIG. 1D illustrates a high level schematic diagram of imaging apparatus 10, with patient 20 illustrated in a seated position and imaging apparatus 10 in an imaging position; FIG. 1E illustrates a high level schematic diagram of imaging apparatus 10, with patient 20 illustrated in a supine position and imaging apparatus 10 in an extended position; and FIG. 1F illustrates a high level schematic diagram of imaging apparatus 10 in an extended position, the figures being described together.

Imaging apparatus 10 comprises: an imager 40; an imager positioner 50; a first imager translation mechanism 60; a second imager translation mechanism 70; a control circuitry 80; and an imager support device 100. FIG. 1A further illustrates an irradiation treatment source 105. FIGS. 1A-1E each further illustrate a patient support positioner 110 in communication with patient support platform 30 and a patient support translation mechanism 120 in communication with patient support positioner 110.

In one embodiment, imager 40 comprises a 3-dimensional imager. In one further embodiment, imager 40 comprises a computed tomography (CT) imager, optionally one of: a closed ring CT imager; an open ring CT imager; and a C-arm CT imager. In another embodiment, as illustrated in FIG. 1F, imager positioner 50 comprises: a support arm 130; an extension arm 140; a rotation member 150; and a rotation ring 160. Support arm 130 is coupled to imager support device 100 and in one embodiment is coupled to first imager translation mechanism 60. Extension arm 140 is coupled to support arm 130 and is arranged to extend therefrom. Rotation member 150 is coupled to rotation ring 160 and rotation ring 160 is coupled to imager 40. In one embodiment, first imager translation mechanism 60 comprises: a screw 170; and a motor 180, screw 170 responsive to the motion of motor 180, however this is not meant to be limiting in any way and screw 170, or the combination of screw 170 and motor 180 can be replaced with any type of translation mechanism, such as a hydraulic device, without exceeding the scope. A first end of screw 170 is coupled to imager 40 and a second end of screw 170 is in communication with motor 180. In another embodiment, second imager translation mechanism 70 comprises: a track 190; a pair of track couplers 200; and an advancement mechanism (not shown), such as a motor and a screw, or a hydraulic device, without limitation, in communication with track couplers 200. In one embodiment, second imager translation mechanism 70 further comprises a pair of support members 210 coupled to each other by a coupling member 220, a first end of coupling member 220 coupled to a first track coupler 200 and a second end of coupling member 220 coupled to a second track coupler 200. In such an embodiment, first imager translation mechanism 60 is coupled to each support member 210 by a respective coupling member 230. Track 190 is coupled to imager support device 100 and in one embodiment is arranged to be parallel to ceiling 253 of a treatment room 250.

In one embodiment, control circuitry 80 is situated within one of the parts of imaging apparatus 10. In another embodiment, control circuitry 80 is in communication with a user input device (not shown) accessible by a user. In one embodiment, imager support device 100 comprises: a pair of support members 260; and a connection member 270. In one embodiment, each support member 260 is attached to ceiling 253 of treatment room 250 and connection member 270 is arranged to connect support members 260 to each other. In another embodiment (not shown), each support member 260 is attached to floor 255 of treatment room 250. Track 190 of second imager translation mechanism 70 is coupled to connection member 270 of imager support device 100.

In one embodiment, patient support positioner 110 comprises a motor 112 and a connecting member 114. In one embodiment, patient support translation mechanism 120 comprises: an elevation member 280; and an extension member 290. A first end of extension member 290 is coupled to elevation member 280 and extension member 290 is arranged to extend from elevation member 280. A first end of connecting member 114 is coupled to a second end of extension member 290 and is arranged to rotate in relation thereto about a first patient rotation axis 320 responsive to the operation of motor 112 in communication with connecting member 114. A second end of connecting member 114 is coupled to patient support platform 30. In one embodiment, patient support positioner 110 further comprises a second motor (not shown) arranged to rotate connecting member 114 about a second patient rotation axis 340, second patient rotation axis 340 generally orthogonal to first patient rotation axis 320. In one further embodiment, second patient rotation axis 340 is generally perpendicular to floor 255 of treatment room 250.

Imager positioner 50 is in communication with imager 40 and control circuitry 80 (connection not shown), and imager 40 is further in communication with first imager translation mechanism 60 and second imager translation mechanism 70. Control circuitry 80 is further in communication with imager 40, first imager translation mechanism 60 and second imager translation mechanism 70 (connection not shown). In one embodiment (not shown), control circuitry 80 is further in communication with patient support positioner 110. In another alternate embodiment, as illustrated in FIG. 1B, an optional control circuitry 240 is provided in communication with patient support positioner 110, optionally further in communication with a user input device (not shown). Optional control circuitry 240 is in communication with control circuitry 80 (connection not shown). Patient support positioner 110 is in one embodiment attached to floor 255 of treatment room 250.

In operation, patient support translation mechanism 120 is controlled, by one of control circuitry 80 and optional control circuitry 240, to translate patient support platform 30 from a first patient position to a second patient position in relation to irradiation treatment source 105. In one embodiment, the first patient position is an initial position at the start of a treatment session and the second patient position is the desired treatment position. In another embodiment, in the event the treatment session includes a plurality of treatment positions, the first patient position is one irradiation treatment position and the second patient position is a different irradiation treatment position. In one embodiment, as illustrated in FIGS. 1A, 1B and 1D, patient support platform 30 is arranged to support patient 20 in a seated position. In another embodiment, as illustrated in FIGS. 1C and 1E, patient support platform 30 is arranged to support patient 20 in a supine position. In one embodiment, elevation member 280 of patient support positioner 110 is rotated around an elevation rotation axis 310 by a motor (not shown) thereby elevating the second end of elevation member 280 and as a consequence elevating patient support platform 30. Extension member 290 is extended by a predetermined length thereby positioning patient support platform 30 into the desired treatment position.

Optional control circuitry 240, or control circuitry 80 is arranged to control patient support positioner 110 to rotate patient support platform 30 about a first patient rotation axis 320 by a patient rotation angle, as illustrated in FIGS. 1B and 1C. In one embodiment, the patient rotation angle is entered by a user at a user input device, and in another embodiment the patient rotation angle is predetermined during a treatment plan. In one embodiment, the patient rotation angle is at least 30 degrees. The rotation of patient support platform 30 about first patient rotation axis 320 brings patient 20 into a desired angle in relation to irradiation treatment source 105.

Control circuitry 80 is arranged to control imager positioner 50 to rotate imager 40 about an imager rotation axis 330 by the patient rotation angle. For example, in the event patient support platform is rotated about first patient rotation axis 320 by 45 degrees, control circuitry 80 is arranged to control imager positioner 50 to rotate imager 40 about imager rotation axis 330 by 45 degrees. In particular, control circuitry 80 is arranged to control extension arm 140 to extend from support arm 30 thereby pushing rotation member 150. The movement of rotation member 150 causes rotation ring 160 to rotate thereby rotating imager 50 about imager rotation axis 330. In the embodiment where the rotation of patient support platform 30 is controlled by optional control circuitry 240, control circuitry 80 is optionally arranged to receive information regarding the patient rotation angle from optional control circuitry 240. In another embodiment, the patient rotation angle is predetermined and stored by control circuitry 80.

Control circuitry 80 is further arranged to control first imager translation mechanism 60 to translate imager 40 a predetermined distance along a first imager translation axis 360. In one embodiment, first imager translation axis 360 is generally perpendicular to floor 255 of treatment room 250. In the embodiment where first imager translation mechanism 60 comprises a screw 170 and a motor 180, control circuitry 80 is arranged to control motor 180 to rotate screw 170 thereby translating imager 40 along first imager translation axis 360.

Control circuitry 80 is further arranged to control second imager translation mechanism 70 to translate imager 40 a predetermined distance along a second imager translation axis 370. In one embodiment, second imager translation axis 370 is generally perpendicular to first imager translation axis 360. In another embodiment, second imager translation axis 370 and first imager translation axis 360 exhibit an angle between each other such that the combination of translation of imager 40 along first imager translation axis 360 and along second imager translation axis 370 causes imager 40 to be translated in the general direction of floor 255 of treatment room 250. In the embodiment where second imager translation mechanism 70 comprises track 190 and track connecting members 200, imager translation axis is parallel to track 190 and control circuitry 80 is arranged to translate second imager translation mechanism 70 along track 190.

The combination of translation of imager 40 along first imager translation axis 360 and second imager translation axis 370 causes imager 40 to be translated along an imaging axis 350, imaging axis 350 being defined by patient support platform 30 and extending the length of the patient support platform 30. In particular, imaging axis 350 is defined as the axis which imager 40 needs to advance along in order to reach a position in which it can image patient 20 supported by patient support platform 30. Imager 40 is translated along imaging axis 350 until reaching an imaging position in relation to patient 20 wherein imager 40 is arranged to image at least a portion of patient 20, as illustrated in FIGS. 1B and 1C. In one embodiment, the translation of imager 40 along first imager translation axis 360 is contemporaneous with the translation of imager 40 along second imager translation axis 370 such that the translation of imager 40 along imaging axis 350 is a generally smooth motion. As imager 40 is translated by second imager translation mechanism 70, first imager translation axis 360 is also translated in the direction of translation of imager 40 along second imager translation axis 370, i.e. first imager translation axis 360 is defined in relation to the current position of imager 40. As imager 40 is translated by first imager translation mechanism 60, second imager translation axis 370 is also translated in the direction of translation of imager 40 along first imager translation axis 360, i.e. second imager translation axis 370 is defined in relation to the current position of imager 40. In one embodiment, when imager 40 is in an imaging position in relation to patient 20, control circuitry 80 is arranged to control imager 40 to image at least a portion of patient 20. In one embodiment, prior to imaging of patient 20, optional control circuitry 240 or control circuitry 80 is arranged to control patient support positioner 110 to rotate patient support platform 30 about second patient rotation axis 340 by a predetermined angle, responsive to a treatment plan.

In one embodiment, prior to the translation of imager 40 along imaging axis 350, as described above, control circuitry 80 is arranged to control one of first imager translation mechanism 60 and second imager translation mechanism 70 to translate imager 40 along the respective first imager translation axis 360 or 370 from a first imager position to a second imager position. In the second imager position, imager 40 is arranged to intersect imaging axis 350, thereby allowing translation of imager 40 there along responsive to the combination of translation along first imager translation axis 360 and second imager translation axis 370, as described above.

In one embodiment, control circuitry 80 is arranged to control the translation and operation of imager 40 along imager translation axis 350 in one of three modes: a helical imaging mode; a single step axial imaging mode; and a double step axial imaging mode. In the helical imaging mode, control circuitry 80 is arranged to control first imager translation mechanism 60 and second imager translation mechanism 70 to continuously translate imager 40 along imaging axis 350. Contemporaneously with the translation of imager 40 along imaging axis 350, control circuitry 80 is further arranged to control imager 40 to image patient 20 when passing over the portion of patient 20 for which imaging is desired. After completion of imaging of the desired portion of patient 20, control circuitry 80 is arranged to cease the imaging of imager 40 and is further arranged to control first imager translation mechanism 60 and second imager translation mechanism 70 to retract imager 40 along imaging axis 350 thereby allowing irradiation of patient 20 by irradiation treatment source 105. In one embodiment, control circuitry 80 comprises an imaging processor and is further arranged to reconstruct a 3 dimensional image of the imaged portion of patient 20 from the helical imaging information received by imager 40, as known in the art of CT imaging. In another embodiment, control circuitry 80 is arranged to transmit the imaging information received by imager 40 to an external processor and in another embodiment imager 40 is arranged to transmit the imaging information to an external processor.

In the single step axial imaging mode, control circuitry 80 is arranged to control first imager translation mechanism 60 and second imager translation mechanism 70 to translate imager 40 along imaging axis 350 until reaching the portion of patient 20 which is to be imaged. Control circuitry 80 is then arranged to control imager 40 to image patient 20. Control circuitry 80 is then arranged to control first imager translation mechanism 60 and second imager translation mechanism 70 to advance imager 40 along imaging axis 350 by a predetermined distance. After the advancement of imager 40 along imaging axis 350, control circuitry 80 is arranged to control imager 40 to image patient 20. Imager 40 is advanced along imaging axis 350, as described, until the entire portion of patient 20 is imaged. After completion of imaging of the portion of patient 20, control circuitry 80 is arranged to cease the imaging of imager 40 and is further arranged to control first imager translation mechanism 60 and second imager translation mechanism 70 to retract imager 40 along imaging axis 350 thereby allowing irradiation of patient 20 by irradiation treatment source 105. In one embodiment, control circuitry 80 comprises an imaging processor and is further arranged to reconstruct a 3 dimensional image of the imaged portion of patient 20 from the plurality of images received by imager 40, as known in the art of CT imaging. In another embodiment, control circuitry 80 is arranged to transmit the imaging information received by imager 40 to an external processor and in another embodiment imager 40 is arranged to transmit the imaging information to an external processor.

In the double step axial imaging mode, control circuitry 80 is arranged to control first imager translation mechanism 60 and second imager translation mechanism 70 to translate imager 40 along imaging axis 350 until reaching the portion of patient 20 which is to be imaged. Control circuitry 80 is then arranged to control imager 40 to image patient 20. Control circuitry 80 is then arranged to control first imager translation mechanism 60 to advance imager 40 along first imager translation axis 360 by a predetermined distance. After the advancement of imager 40 along first imager translation axis 360, control circuitry 80 is arranged to control imager 40 to image patient 20. Control circuitry 80 is then arranged to control second imager translation mechanism 70 to advance imager 40 along second imager translation axis 370 by a predetermined distance. After the advancement of imager 40 along second imager translation axis 370, control circuitry 80 is arranged to control imager 40 to image patient 20. As described above, the combination of translation of imager 40 along first imager translation axis 360 and along second imager translation axis 370 causes translation of imager 40 along imaging axis 350. During imaging processing, the image of patient 20 taken after translation along first imager translation axis 360 is combined with the image of patient 20 taken after translation along second imager translation axis 370 to create a single 3 dimensional image. Imager 40 is advanced along imaging axis 350, as described, until the entire portion of patient 20 is imaged. After completion of imaging of the portion of patient 20, control circuitry 80 is arranged to cease the imaging of imager 40 and is further arranged to control first imager translation mechanism 60 and second imager translation mechanism 70 to retract imager 40 along imaging axis 350 thereby allowing irradiation of patient 20 by irradiation treatment source 105. In one embodiment, control circuitry 80 comprises an imaging processor and is further arranged to reconstruct a 3 dimensional image of the imaged portion of patient 20 from the plurality of images received by imager 40, as known in the art of CT imaging. In another embodiment, control circuitry 80 is arranged to transmit the imaging information received by imager 40 to an external processor and in another embodiment imager 40 is arranged to transmit the imaging information to an external processor.

In one embodiment, in the event the patient rotation angle is 0 degrees, i.e. patient support platform 30 is not rotated about first patient rotation axis 320, the translation of imager 40 along first imager translation axis 360 is separate from the translation of imager 40 along second imager translation axis 370. Particularly, in the event patient 20 is in a seated position, as illustrated in FIG. 1D, control circuitry 80 is arranged to control second imager translation mechanism 70 to translate imager 40 along second imager translation axis 370 until first imager translation axis 360 meets with imaging axis 350. Control circuitry 80 is then arranged to control first imager translation mechanism 60 to translate imager 40 along first imager translation axis 360 until imager 40 reaches patient 20, as described above. In the event patient 20 is in a supine position, as illustrated in FIG. 1E, control circuitry 80 is arranged to control first imager translation mechanism 60 to translate imager 40 along first imager translation axis 360 until second imager translation axis 370 meets with imaging axis 350. Control circuitry 80 is then arranged to control second imager translation mechanism 70 to translate imager 40 along second imager translation axis 370 until imager 40 reaches patient 20, as described above.

After completion of imaging of patient 20, the position of patient 20 can be adjusted with patient support positioner 110 and patient support translation mechanism 120 so as to allow greater accuracy of positioning in relation to treatment irradiation source 105.

Figure 2A:
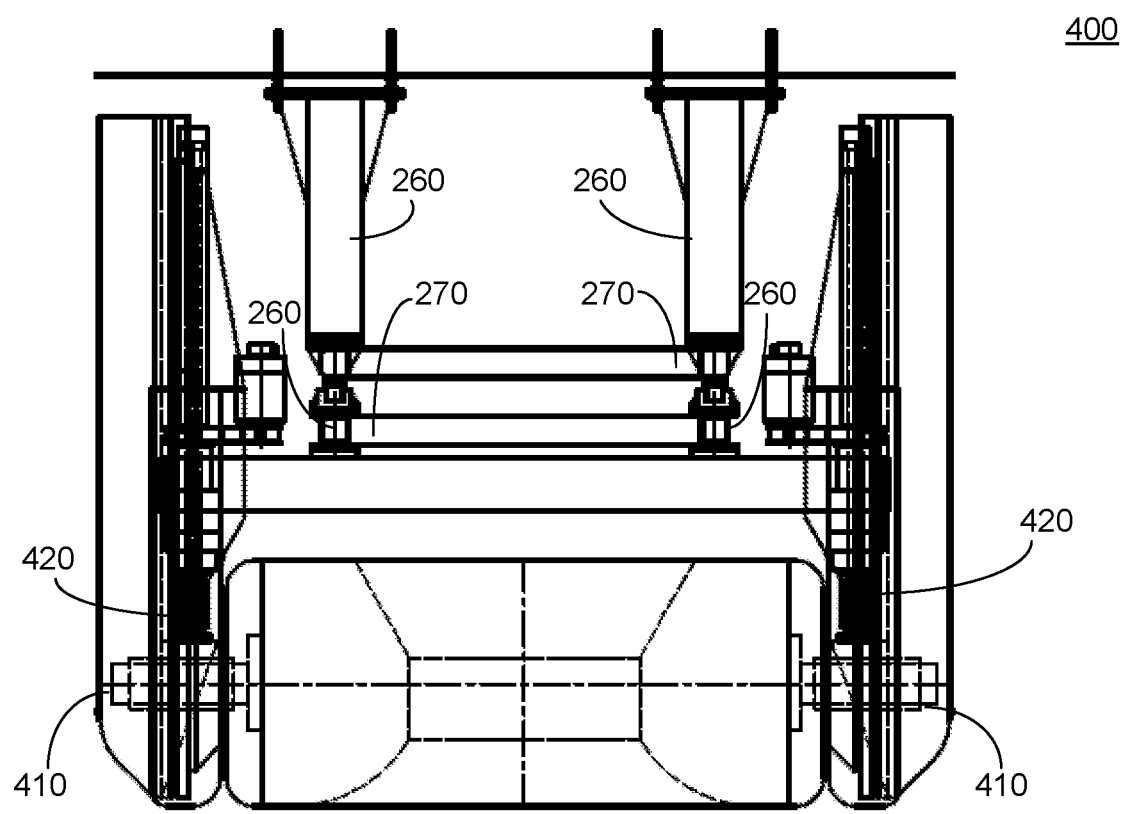
FIGS. 2A-2D illustrate a high level schematic diagram of various positions a first embodiment of an imaging apparatus for use with a patient supported by a patient support platform.
Figure 2B:
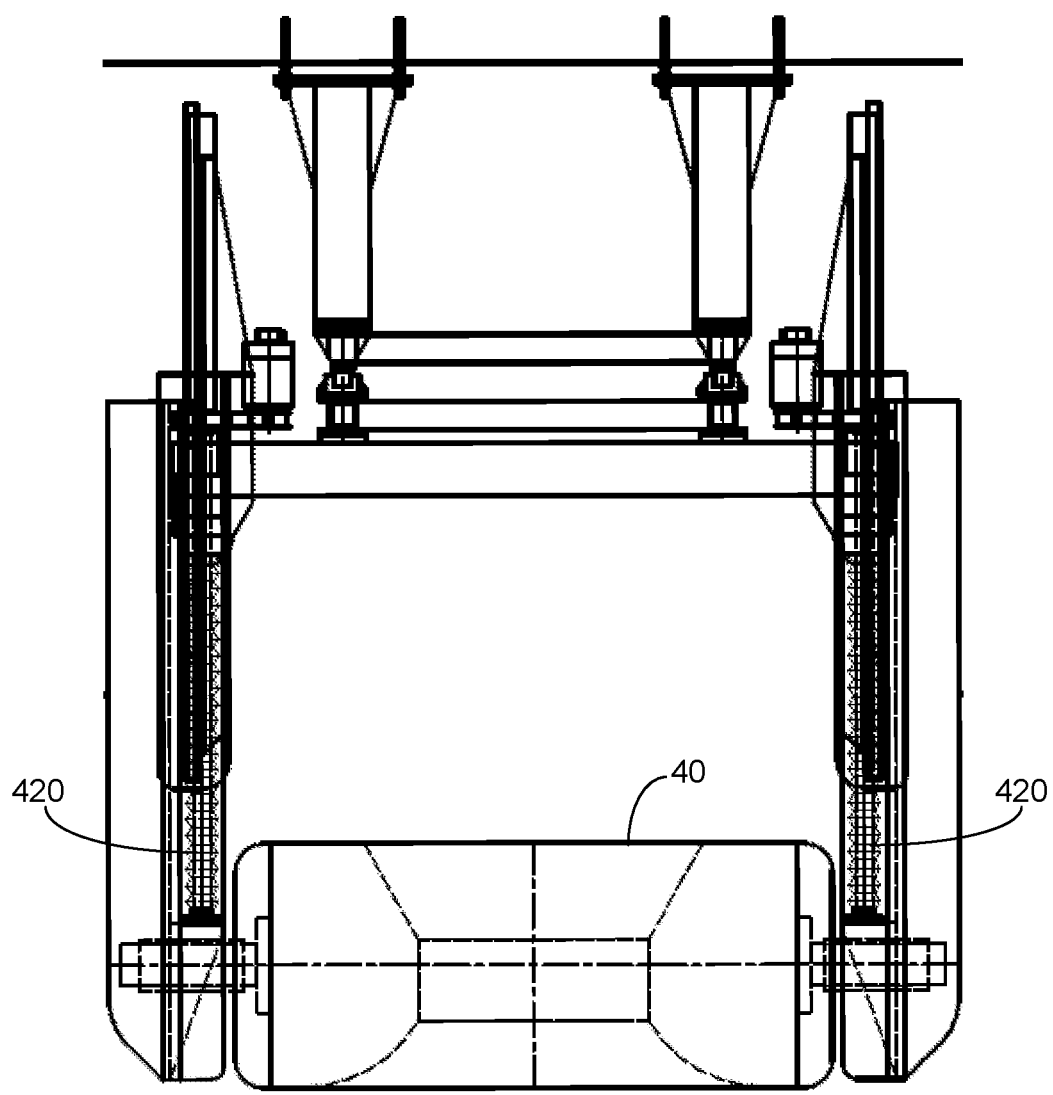
Figure 2C:
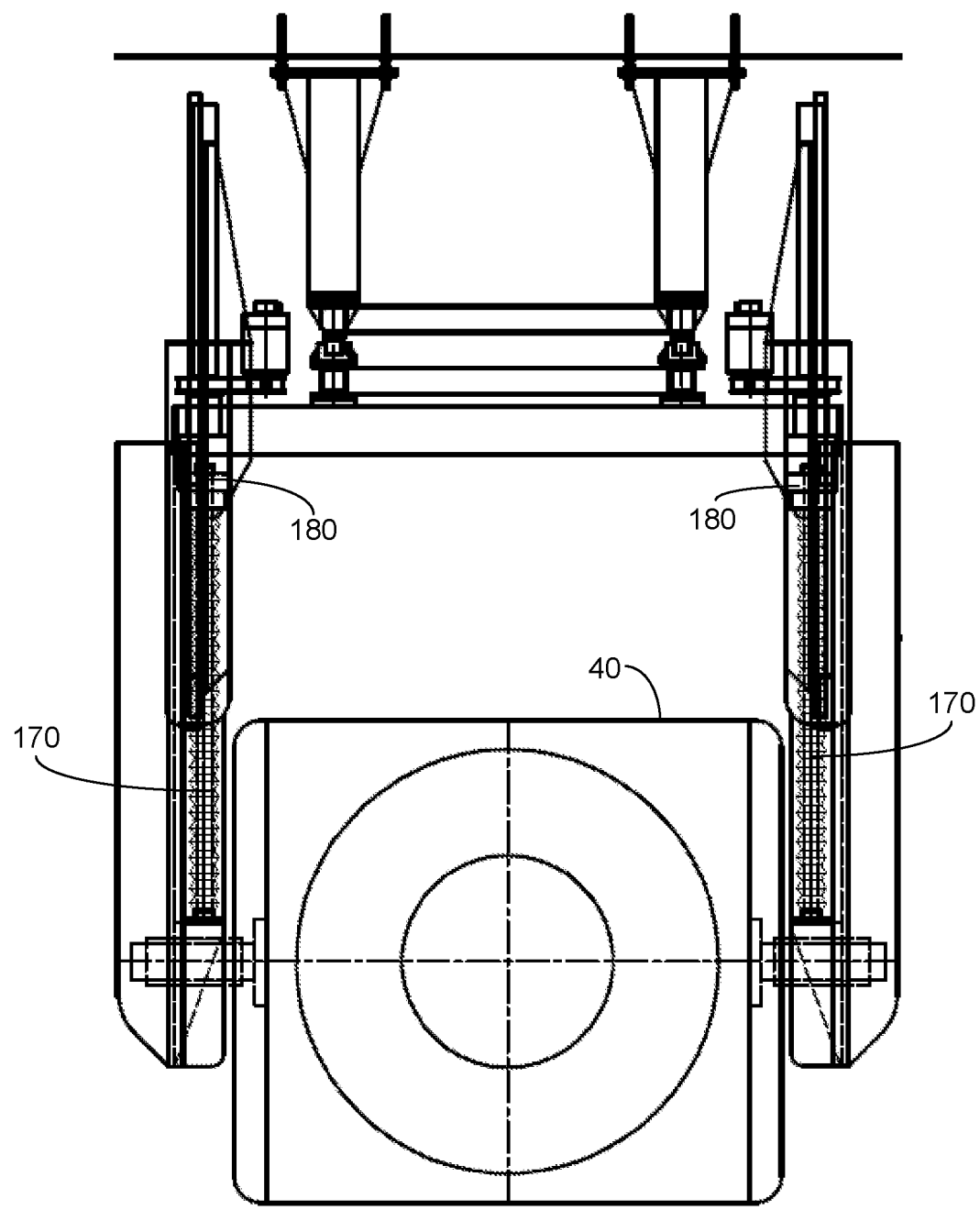
Figure 2D:
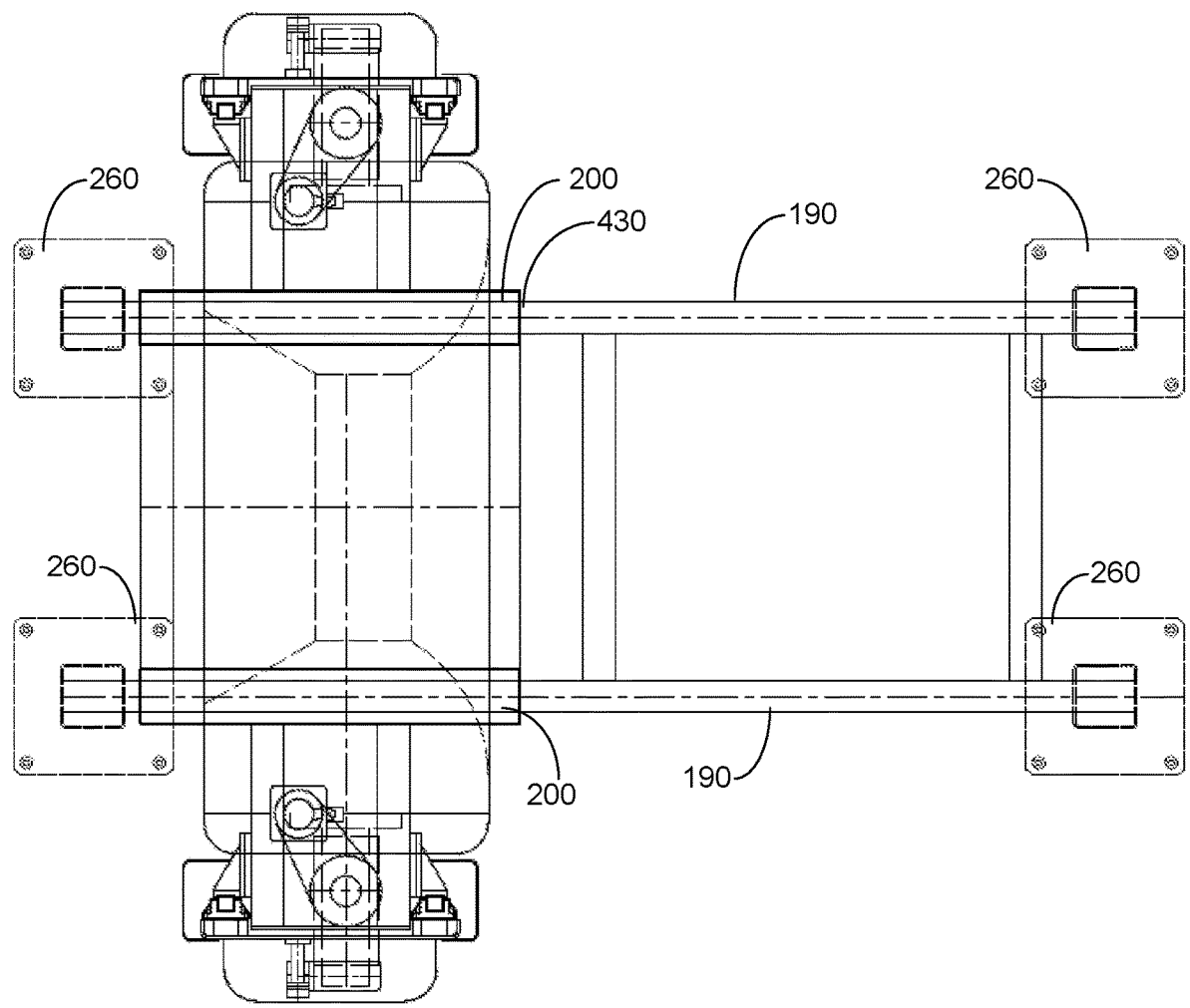

FIG. 2A illustrates a high level schematic diagram of a side view of an apparatus 400 for providing imaging of a patient in a contracted position; FIG. 2B illustrates a high level schematic diagram of a side view of apparatus 400 in a partially extended position; FIG. 2C illustrates a high level schematic diagram of a side view of apparatus 400 in a fully extended position; and FIG. 2D illustrates a top view apparatus 400. Apparatus 400 comprises: an imager 40; a pair of imager positioners 410; a pair of imager translation mechanisms 420; a imager translation mechanism 430; a control circuitry 80; and an imager support device 440. In one embodiment, each imager positioner 410 comprises a motor, in communication with control circuitry 80 (connection not shown) and coupled to one side of imager 40. In another embodiment (not shown), each imager positioner 410 is coupled to one side of imager 40 and comprises: a support arm; an extension arm; a rotation member; and a rotation ring, as described above in relation to imager positioner 50. In one embodiment, each imager translation mechanism 420 comprises: a screw 170; and a motor 180, however this is not meant to be limiting in any way and screw 170 can be replaced with any typed of translation mechanism, such as a hydraulic device, without exceeding the scoped. A first end of screw 170 is coupled to one side of imager 40, optionally to a motor 450 coupled to imager 40. A second end of screw 170 is coupled to the respective motor 180.

In one embodiment, imager translation mechanism 430 comprises: a pair of tracks 190; a pair of track couplers 200, each arranged to advance along a particular track 200; and an advancement mechanism (not shown), such as a motor and a screw, or a hydraulic device, without limitation, coupled to track couplers 200. In another embodiment, imager support device 440 comprises: a plurality of support members 260; and a pair of connection beams 270, each connection member 270 arranged to connect a pair of support members 260. In one embodiment, each support member 260 is attached to ceiling 253 of treatment room 250. Each track 190 of imager translation mechanism 430 is coupled to a particular connection member 270. In one embodiment, control circuitry 80 is situated within one of the parts of imaging apparatus 10. In another embodiment, control circuitry 80 is in communication with a user input device (not shown) accessible by a user. The operation of apparatus 400 is in all respects similar to imaging apparatus 10 of FIGS. 1A-1F and in the interest of brevity will not be further described.

FIG. 3 illustrates a high level flow chart of a method of providing imaging of a patient supported by a patient support platform, such as patient 20 supported by patient support platform 30. In stage 1000, an imager, such as imager 40, is rotated about an imager rotation axis, such as imager rotation axis 330, by a patient rotation angle. The patient rotation angle is the angle of rotation of the patient support platform about a first patient rotation axis. Optionally, the patient rotation angle is at least 30 degrees. Optionally, the imager is one of: a closed ring CT imager; an open ring CT imager; and a C-arm CT imager.

In stage 1010, the imager is translated along a first imager translation axis. In one embodiment, as described above in relation to first imager translation axis 360 of FIGS. 1A-1F, the first imager translation axis is generally perpendicular to the floor of a treatment room. In stage 1020, the imager is translated along a second imager translation axis, different than the first imager translation axis of stage 1010, and preferably orthogonal thereto. In one embodiment, as described above, in relation to second imager translation axis 370 of FIGS. 1A-1F, the second imager translation axis is generally parallel to the floor of the treatment room. Optionally, the translation of the imager along the second imager translation axis is contemporaneous with the translation of the imager along the first imager translation axis of stage 1010. The combination of the translation of the imager along the first imager translation axis of stage 1010 and the translation of the imager along the second imager translation axis causes the imager to be translated along an imaging axis defined by patient support platform 30. In particular, the imaging axis is defined as the axis which the imager needs to advance along in order to reach a position in which it can image the patient supported by the patient support platform.

In optional stage 1030, a patient support positioner is provided, such as patient support positioner 110, which is controlled to rotate the patient support platform about the first patient rotation axis by the patient rotation angle. In optional stage 1040, the patient support positioner of optional stage 1030 is further controlled to rotate the patient support platform about a second patient rotation axis, such as second patient rotation axis 340, by a predetermined angle responsive to a treatment plan, the second patient rotation axis generally orthogonal to the first patient rotation axis. In optional stage 1050, the patient support platform is translated from a first patient position to a second patient position in relation to a treatment irradiation source, the second patient position removed from the first patient position by at least two, preferably orthogonal, dimensions. In optional stage 1060, the imager of stage 1000 is translated along one of the first imager translation axis of stage 1010 and the second imager translation axis of stage 1020 from a first imager position to a second imager position. In the second imager position, the imager is arranged to intersect the imaging axis of stage 1020.

Figure 4A:
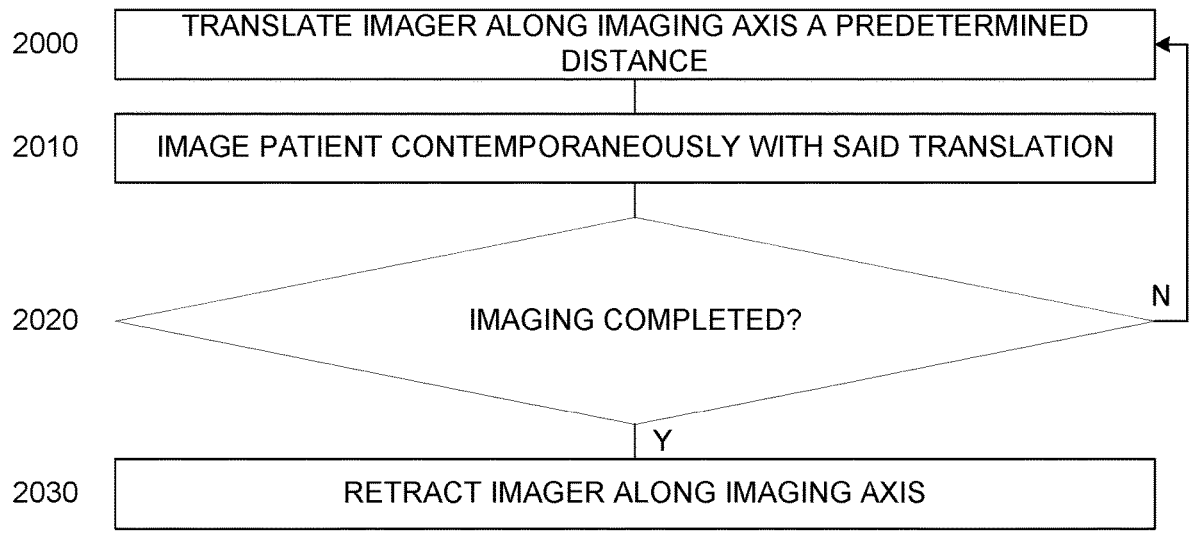
FIGS. 4A-4C illustrate high level flow chart of various methods of imaging a patient.

FIG. 4A illustrates a high level flow chart of a method of imaging a patient supported by a patient support platform in a helical mode of an imager. In stage 2000, an imager is translated along an imaging axis by a predetermined distance responsive to translation of the imager along a first imager translation axis and along a second translation axis, as described above. As described above, the imaging axis is defined by the patient support platform. In stage 2010, the imager is arranged to image the patient contemporaneously with the translation of stage 2000. In stage 2020, it is determined whether imaging has been completed of the entire portion of the patient which is desired to be imaged. In the event that the imaging is not completed, the translating of stage 2000 is continued. In the event that the imaging is completed, in stage 2030 the imaging is ceased and the imager is retracted along the imaging axis. As described above, the acquired imaging information of stage 2010 is processed and a 3 dimensional image is produced.

Figure 4B:
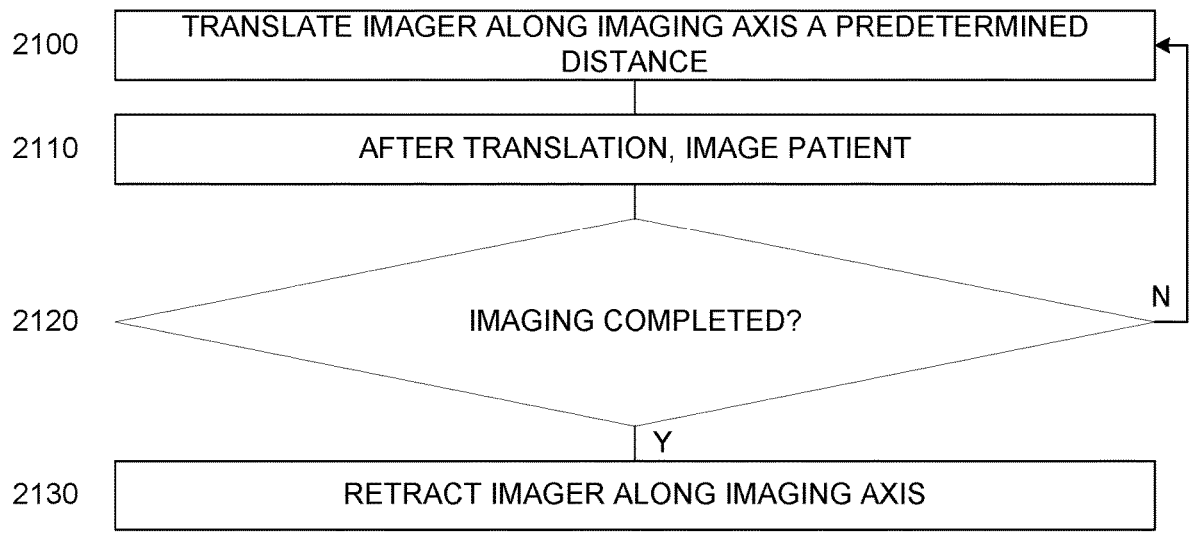

FIG. 4B illustrates a high level flow chart of a method of imaging a patient supported by a patient support platform in a single step axial mode of an imager. In stage 2100, an imager is translated along an imaging axis by a predetermined distance responsive to translation of the imager along a first imager translation axis and along a second translation axis, as described above. As described above, the imaging axis is defined by the patient support platform. In stage 2110, after translation of the imager by the predetermined distance of stage 2100, the imager is arranged to image the patient. In stage 2120, it is determined whether imaging has been completed of the entire portion of the patient which is desired to be imaged. In the event that the imaging is not completed, stage 2100 is repeated. In the event that the imaging is completed, in stage 2130 the imaging is ceased and the imager is retracted along the imaging axis. As described above, the acquired imaging information of stage 2110 is processed and a 3 dimensional image is produced.

Figure 4C:
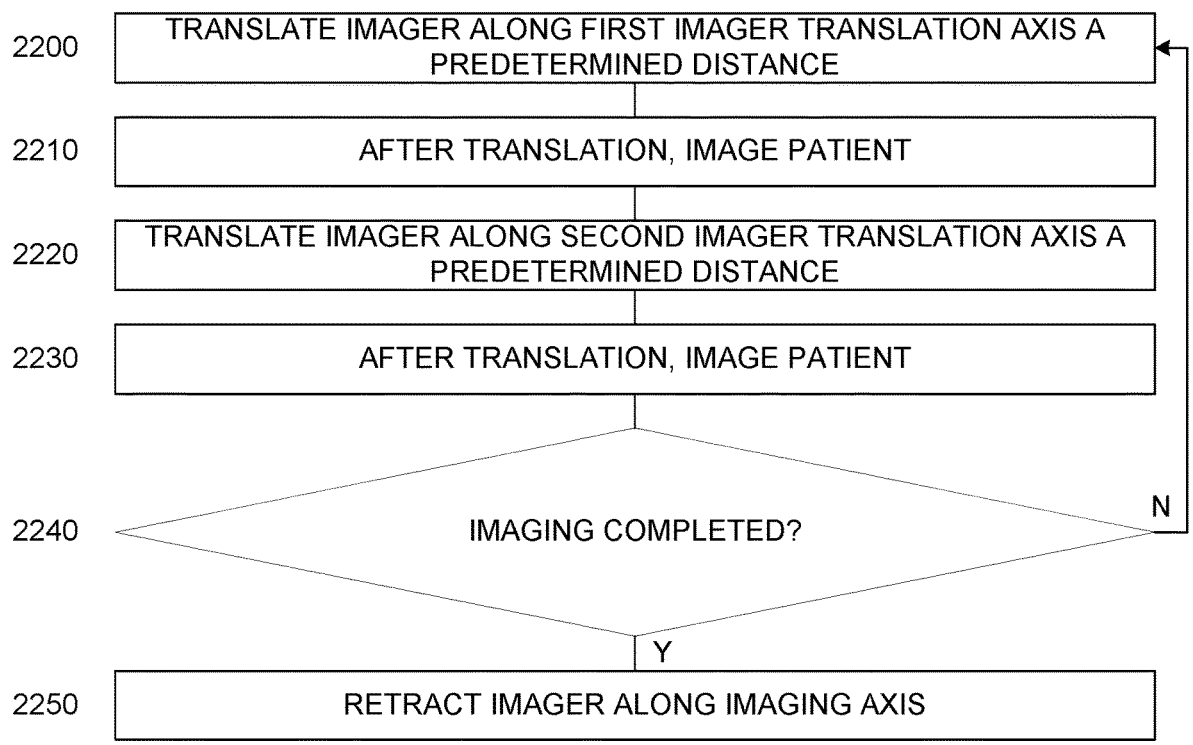

FIG. 4C illustrates a high level flow chart of a method of imaging a patient supported by a patient support platform in a double step axial mode of an imager. In stage 2200, an imager is translated along a first imager translation axis by a predetermined distance, as described above. In stage 2210, after translation of the imager by the predetermined distance of stage 2200, the imager is arranged to image the patient. In stage 2220, an imager is translated along a second imager translation axis by a predetermined distance, as described above. In stage 2230, after translation of the imager by the predetermined distance of stage 2220, the imager is arranged to image the patient. As described above, the combination of the translation of stage 2000 and the translation of stage 2220 causes the imager to be translated along an imaging axis defined by the patient support platform. As further described above, the received image of stage 2210 and the received image of stage 2230 are combined together to produce a single 3 dimensional image. In stage 2240, it is determined whether imaging has been completed of the entire portion of the patient which is desired to be imaged. In the event that the imaging is not completed, stage 2200 is repeated. In the event that the imaging is completed, in stage 2250 the imaging is ceased and the imager is retracted along the imaging axis. As described above, the acquired imaging information of stages 2210 and 2230 is processed and a 3 dimensional image is produced.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

We claim:
1. An imaging apparatus comprising:
a patient support platform comprising a patient support positioner arranged to be rotated about a first patient rotation axis by a patient rotation angle;
a 3 dimensional (3D) imager comprising one of: a closed ring computed tomography (CT) imager and an open ring CT imager;
an imager positioner in communication with said 3D imager and arranged to rotate said 3D imager about an imager rotation axis,
wherein the imager positioner comprises:
a support arm, coupled to an imager support device;
an extension arm; and
rotation member coupled to a rotation ring connected to said 3D imager;
a first imager translation mechanism coupled to said 3D imager and arranged to translate said 3D imager along a first imager translation axis,
wherein the first imager translation mechanism comprises:
a first screw and a first motor; or
a first hydraulic device;
a second imager translation mechanism in communication with said 3D imager and arranged to translate said 3D imager, along a second imager translation axis different than said first imager translation axis, wherein the second imager translation mechanism comprises:
a plurality of treatment room support members, connectable to one of: a ceiling or a floor of a treatment room;
two or more tracks, assembled parallel to the second imager translation axis, such that each track is coupled to two support members via two or more connection beams;
one or more first imager translation mechanism support members, coupled to the first imager translation mechanism from one end, and to one track, from the two or more tracks, from the other end; and an advancing mechanism comprising: a second motor and a second screw, or a second hydraulic device; and
a control circuitry in communication with said patient support positioner, said imager positioner, said first imager translation mechanism and said second imager translation mechanism, and arranged to:
prior to imaging the patient, bring said patient support platform to a first predetermined position and a first predetermined orientation with respect to said 3D imager;
control said imager positioner to rotate said 3D imager about said imager rotation axis by the patient rotation angle;
control said first imager translation mechanism to translate said 3D imager along said first imager translation axis; and
control said second imager translation mechanism to translate said 3D imager along said second imager translation axis,
wherein the combination of said translation of said 3D imager along said first imager translation axis and along said second imager translation axis causes said 3D imager to be translated along an imaging axis, such that said 3D imager intersects said imaging axis and such that said 3D imager is arranged to image the patient supported by the patient support platform, and
wherein said imaging axis is defined by the patient support platform and extends along a length of the patient support platform, and
wherein said control circuitry is further arranged to control said 3D imager to image the patient contemporaneously with said translation along said imaging axis.

2. The imaging apparatus of claim 1, wherein the patient support positioner is arranged to rotate the patient support platform about the first patient rotation axis,
wherein said control circuitry is further arranged to control said patient support positioner to rotate said patient support platform about the first patient rotation axis by the patient rotation angle.

3. The imaging apparatus of claim 1, further comprising a patient support translation mechanism arranged to translate said patient support platform from a first patient position to any of a plurality of second patient positions such that the patient supported by said patient support platform is in a predetermined position,
wherein, in said second patient position, the patient support platform is removed from said first patient position in at least two dimensions,
wherein, prior to said translation of said imager along said imaging axis, said control circuitry is further arranged to control one of said first imager translation mechanism and said second imager translation mechanism to translate said 3D imager, along said respective one of said first imager translation axis and said second imager translation axis, from a first imager position to a second imager position,
wherein said intersection of said 3D imager with said imaging axis is in said second imager position.

4. The imaging apparatus of claim 1, wherein said first patient rotation axis is generally parallel to the ground.

5. The imaging apparatus of claim 1, wherein said translation of said 3D imager along said first imager translation axis is contemporaneous with said translation of said imager along said second imager translation axis.

6. The imaging apparatus of claim 1, wherein the first patient rotation angle is at least 30 degrees.

7. The imaging apparatus of claim 1, wherein said 3D imager comprises one of: a close ring computed tomography imager; an open ring computed tomography imager; and a C-arm computed tomography imager.

8. The imaging apparatus of claim 1, wherein said control circuitry is further arranged to alternately:
control said first imager translation mechanism and said second imager translation mechanism to translate said 3D imager along said imaging axis by a predetermined distance; and
control said 3D imager to image the patient.

9. The imaging apparatus of claim 1, wherein said control circuitry is further arranged to alternately:
control said first imager translation mechanism to translate said 3D imager along said first imager translation axis;
control said 3D imager to image the patient;
control said second imager translation mechanism to translate said 3D imager along said second imager translation axis; and
control said 3D imager to image the patient.

10. The imaging apparatus of claim 1, wherein said imaging axis is defined as the axis which said 3D imager needs to advance along in order to reach a position in which it can image the patient supported by said patient support platform.

11. A method of providing imaging of a patient supported by a patient support platform arranged to be rotated about a first patient rotation axis by a patient rotation angle, the method comprising:
prior to imaging the patient, bringing said patient support platform to a first predetermined position and a first predetermined orientation with respect to said 3D imager;
rotating a 3 dimensional (3D) imager about an imager rotation axis by the patient rotation angle, using imager positioner comprising:
a support arm, coupled to an imager support device;
an extension arm;
rotation member coupled to a rotation ring connected to said 3D imager;
translating said 3D imager along a first imager translation axis, using a first imager translation mechanism comprising:
a first screw and a first motor; or
a first hydraulic device;
translating said 3D imager along a second imager translation axis different than said first imager translation axis, using second imager translation mechanism comprising:
a plurality of treatment room support members, connectable to one of: a ceiling or a floor of a treatment room;
two or more tracks, assembled parallel to the second imager translation axis, such that each track is coupled to two support members via two or more connection beams;
one or more first imager translation mechanism support members, coupled to the first imager translation mechanism from one end, and to one track, from the two or more tracks, from the other end; and
an advancing mechanism comprising: a second motor and a second screw, or a second hydraulic device; and
controlling said 3D imager to image the patient contemporaneously with said translation along said imaging axis,
wherein the combination of said translation of said 3D imager along said first imager translation axis and along said second imager translation axis causes said 3D imager to be translated along an imaging axis, such that said 3D imager intersects said imaging axis and such that said 3D imager is arranged to image the patient supported by the patient support platform, and wherein said imaging axis is defined by the patient support platform and extends along a length of the patient support platform.

12. The method of claim 11, further comprising rotating the patient support platform about the first patient rotation axis by the patient rotation angle.

13. The method of claim 11, wherein said translating said 3D imager along said first imager translation axis is contemporaneous with said translating said 3D imager along said second imager translation axis.

14. The method of claim 11, wherein the patient rotation angle is at least 30 degrees.

15. The method of claim 11, further comprising:
translating the patient support platform from a first patient position to any of a plurality of second patient positions, such that the patient supported by the patient support platform is in a predetermined position in relation to an irradiation treatment source; and
prior to said translating said 3D imager along said imaging axis, translating said 3D imager along one of said first imager translation axis and said second imager translation axis from a first imager position to a second imager position,
wherein, in said second patient position, the patient support platform is removed from said first patient position in at least two dimensions, and
wherein said intersection of said 3D imager with said imaging axis is in said second imager position.

16. The method of claim 11, wherein said 3D imager comprises one of: a closed ring computed tomography imager; an open ring computed tomography imager; and a c-arm computed tomography imager.

17. The method of claim 11, further comprising imaging the patient contemporaneously with said translating along said imaging axis.

18. The method of claim 11, wherein said imaging axis is defined as the axis which said 3D imager needs to advance along in order to reach a position in which it can image the patient supported by the patient support platform.

* * * * *